United States Patent
Fabritius et al.

(10) Patent No.: US 7,365,219 B2
(45) Date of Patent: Apr. 29, 2008

(54) SOLID PHASE EXTRACTION METHOD FOR OBTAINING HIGH-PURITY UNSATURATED COMPOUNDS OR DERIVATIVES OF SAID COMPOUNDS

(75) Inventors: Dirk Fabritius, Mainz (DE); Silke Reimann, Ansbach (DE); Doreen Neumann, Hofheim (DE); Daniel Minoer, Frankfurt am Main (DE)

(73) Assignee: Nutrinova Nutrition Specialties & Food Indredients GmbH (DE)

( * ) Notice: Subject to any disclaimer, the term of this patent is extended or adjusted under 35 U.S.C. 154(b) by 772 days.

(21) Appl. No.: 10/479,620

(22) PCT Filed: Jun. 5, 2002

(86) PCT No.: PCT/EP02/06158

§ 371 (c)(1),
(2), (4) Date: Dec. 4, 2003

(87) PCT Pub. No.: WO02/098826

PCT Pub. Date: Dec. 12, 2002

(65) Prior Publication Data

US 2004/0162437 A1    Aug. 19, 2004

(30) Foreign Application Priority Data

Jun. 5, 2001    (DE) ................................ 101 27 111

(51) Int. Cl.
*C07C 67/52*    (2006.01)
(52) U.S. Cl. .................. 554/193; 562/608; 568/917

(58) Field of Classification Search ................ 554/185, 554/193; 562/608; 568/917
See application file for complete search history.

(56) References Cited

U.S. PATENT DOCUMENTS 4,189,442 A * 2/1980 Lubsen et al. .............. 554/187
4,721,584 A   1/1988 Arai et al.

FOREIGN PATENT DOCUMENTS

FR    2 650 274 A1    1/1991

OTHER PUBLICATIONS

R.O. Adolf et al., "The Isolation of Omega-3 Polyunsaturated Fatty Acids and Methyl Esters of Fish Oils by Silver Resin", Jaocs, Nov. 1985, pp. 1592-1595, vol. 62, No. 11.
R.O. Adolf et al., "Partial Argentation Resin Chromatography (PARC): I. Effect of Percent Silver on Elution and Separation of Methyl Octadecadienoate Isomers", Jaocs, Sep. 1980, pp. 273-275.
W.J. DeJarlais et al., "Acetonitrile as Eluent in Silver Resin Column Chromatography", Jaocs, May 1983, pp. 975-978, vol. 60, No. 5.

* cited by examiner

*Primary Examiner*—Arun S. Phasge
(74) *Attorney, Agent, or Firm*—Hammer & Hanf, P.C.

(57) ABSTRACT

The invention relates to a novel extraction method for obtaining at least one unsaturated, optionally derivatized compound, from mixtures of said compounds with other less saturated constituents, e.g. for obtaining polyunsaturated fatty acids or the derivatives thereof from mixtures with saturated and/or less unsaturated, optionally derivatized fatty acids, by means of selective complexation with a cation exchanger which is partially or fully charged with silver ions, and subsequent decomplexation.

22 Claims, 3 Drawing Sheets

Figure 1:
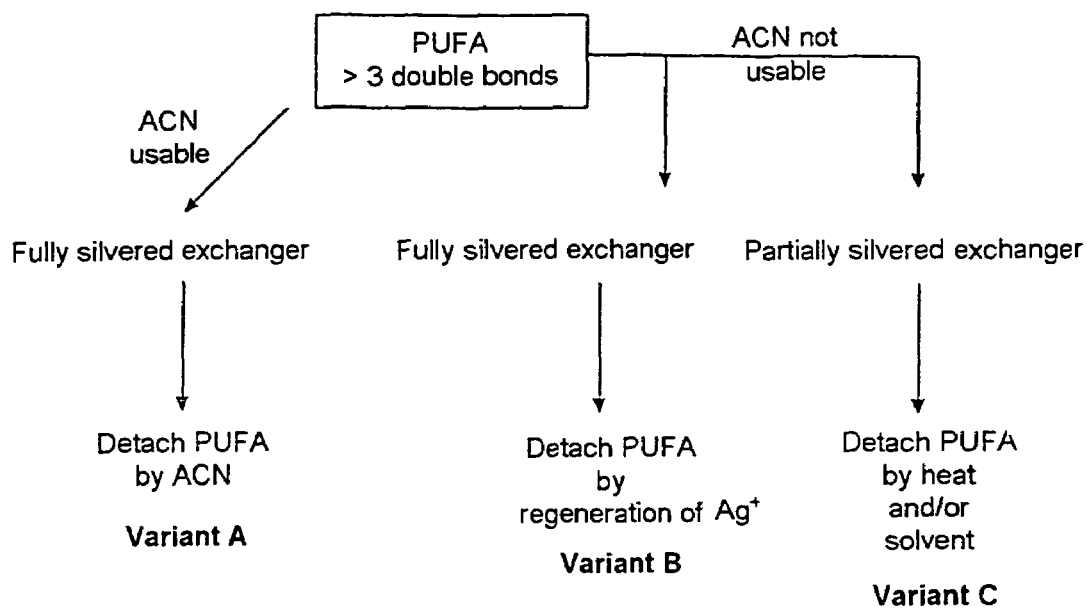

SOLID PHASE EXTRACTION METHOD FOR OBTAINING HIGH-PURITY UNSATURATED COMPOUNDS OR DERIVATIVES OF SAID COMPOUNDS

This application is a 371 of PCT/EP02/06158, filed Jun. 5, 2002, the entirety of which is hereby incorporated by reference.

The present invention relates to a novel extraction method for obtaining one or more unsaturated, derivatized or underivatized compounds from mixtures of these with other less highly saturated components, for example obtaining polyunsaturated fatty acids or derivatives thereof from mixtures with saturated and/or less highly unsaturated, derivatized or underivatized fatty acids, by selective complexation at a cation exchanger which is partially or completely loaded with silver ions; and subsequent decomplexation.

Polyunsaturated long-chain fatty acids (PUFAS) are essential fatty acids in human metabolism. PUFAs can be subdivided into two large groups. In addition to the group of ω-6 PUFAs, the formula of which is based on linoleic acid, there is the group of ω-3 PUFAS, which is builtup, on the basis of α-linolenic acid.

PUFAs are important building blocks of cell membranes, the retina and the meninges and are precursors of important hormones, for example prostaglandins, thromboxanes and leukotrienes.

In addition to the function of building blocks, in the course of recent years, it has increasingly frequently been found that PUFAs directly have a variety of beneficial effects on the human body or disorders.

A multiplicity of clinical studies have found that PUFAs, in the case of, for example, cancer, rheumatoid arthritis, hypertension and neurodermatitis and many other disorders, can make an important contribution toward healing or relief. These findings were causally responsible for the fact that international institutions and authorities have made recommendations controlling the daily intake of PUFAs.

PUFAs cannot be synthesized by humans de novo, since they lack the enzyme systems which can introduce a double bond at the >C9 position in the carbon chain (missing Δ12 desaturase). Humans are only able to synthesize polyunsaturated fatty acids when there is a supply of precursor fatty acids (for example α-linolenic acid) via the diet. However, there is some dispute as to whether this amount is sufficient to cover the requirement of polyunsaturated fatty acids.

The great majority of essential fatty acids are consumed via the diet. In-particular vegetable oils are enriched with ω-6 fatty acids (for example evening primrose oil contains γ-linolenic acid (GLA)), but only up to a chain length of C18, and fish oils or oils from microorganisms containing ω-3 fatty acids (for example salmon oil contains eicosapentaenoic acid (EPA) and docosahexaenoic acid (DHA)). In principle, fish oils and oils from microorganisms are the sole commercial source of polyunsaturated fatty acids. However, generally, the content of the desired PUFA is low and this is present in a mixture, in which case PUFAs which have an antagonistic action can likewise be present. In order to consume the recommended daily allowance of PUFAs, a large amount of oil must be consumed. In particular, this affects those patients who have to consume high doses of PUFAs (for example in the case of cystic fibrosis). To achieve an effect of the individual PUFAs which is as targeted as possible, enriched or high-purity PUFAs must be used. There is therefore a great requirement for high-purity PUFAs in the prior art.

The use of silver-loaded cation exchangers for purifying and separating unsaturated fatty acids in analytical chromatography systems (column chromatography) has already been described.

Use is made here not only of HPLC [Adlof, R. O. and E. A. Emken (1985): *The isolation of omega-3 polyunsaturated fatty acids and methyl esters of fish oil by silver resin chromatography*. JAOCS, 62(11), 1592-1595; Christie, W. W. (1987): *A stable silver loaded column for the separation of lipids by high performance liquid chromatography*. J. of High resolution Chromatography & Chromatography Communications, 10, 148-150], SFC [Kadota, Yasuhiko; Tanaka, Isao; Ohtsu, Yutaka; Yamaguchi, Michihiro (1998): *Separation of polyunsaturated fatty acids by chromatography using a silver-loaded spherical clay. II Industrial-scale preparation of high purity DHA*. Nihon Yyugakkaaishi, 47(4), 351-357] and column chromatography systems [Nieto, S.; Ana M Cordoba; J. Sanhueza and A. Velenzueela (1997): *Obtention of highly purified fractions of eicosapentaenoic acid and docosahexaenoic acid from sardine oil by silver-resin chromatography: A semi-preparative procedure*. Grasas y Aceites, 48(4), 197-199; Belarbi, El Hassan; Emilio Molina and Yusuf Chisti (2000): *A process for high yield and scalable recovery of high purity eicosapentaenoic acid esters from microalgae*. Enzyme and Microbial Technology, 26, 516-529] with silica gels but also of ion exchangers. This applies, in particular, to analytical methods.

A further chromatography method is ligand-exchange chromatography (LEC). This has been used particularly in systems where no PUFAs are to be separated [Pyell, U., S. Schober and G. Stork (1997): *Ligand-exchange chromatographic separation of polycyclic aromatic hydrocarbons and polycyclic aromatic sulfur heterocycles on a chelating silica gel loaded with palladium (II) or silver (I) cations*. Fresenius J Anal Chem., 359, 538-541; Janak, K., M. Demirbueker, I. Haegglund and L. G. Blomberg (1992): *Modifications of poly(methyl-3-propylthiol)siloxane to give stationary phases for open tubular supercritical fluid chromatography*. Chromatographia, 34(5-8), 335-341].

Silver-loaded cation exchanger systems are used in the application JP 45021376, where Dowex® 50 is described as a chromatography material for purifying ethyl ester mixtures based on evening primrose oil. A pure GLAEE fraction (GLAEE=γ-linolenic acid ethyl ester) was successfully isolated in 78% yield.

In all systems the problem occurs that the polyunsaturated fatty acids can be eluted from the column only extremely slowly and poorly (Adlof, R. O.; H. Rakoff and E. A. Emken (1980): *Partial Argentation Resin Chromatography (PARC): I. Effect of Percent Silver on Elution and Separation of Methyl Octadecadienoate Isomers*. JAOCS, 9, 273-275). In this case, high amounts of solvent are consumed. Furthermore, fractionation steps are required to separate the purified product fractions.

Only the use of pure acetonitrile (ACN) or mixtures with acetonitrile has led to an acceptable elution time (Dejarlais, W. J.; R. O. Adlof and E. A. Emken (1983): *Acetonitrile as Eluent in Silver Resin Column Chromatography*. JAOCS, 60(5), 975-978). Here, generally gradient systems are used which make regenerating the solvents more difficult.

For industrial use, large amounts of acetonitrile, owing to the high cost and the toxicological risk (acetonitrile can contain prussic acid (HCN)), are highly unsuitable.

Scaling up the chromatographic methods, and thus industrial use, is also only possible with limitations, owing to the column dimensions to be used.

Adlof et al (1980, above) have produced partially silvered cation exchangers which made it possible to elute esters of diunsaturated fatty acids using alcohols as eluents. More highly unsaturated fatty acids have not been used. However, it must be assumed that likewise in this case, without acetonitrile, elution is not possible.

It is reported that, starting from fish oils for production by means of SFC, costs of $550/kg of DHAEE arise [Alkio, M.; C. Gonzalez; M. Jäntti and O. Altonen (2000): *Purification of polyunsaturated fatty acid esters from Tuna oil with supercritical fluid chromatography*. JAOCS, 77(3), 315-321]. Here, a production rate of approximately 0.5 g of DHAEE per kg of stationary phase and hour is mentioned. This is equivalent to a loading (DHAEE/stationary phase) of 0.05%. The capital costs of the SFC equipment are $2 million.

An SFC production method is likewise known using a silver-loaded matrix starting from fish oil, in which DHAEE can be produced for $4 000/kg [Tanaka, Isao (1996): *Supercritical chromatography facilitates fatty acid production*. Chem. Eng. April, 19-21].

Yamamura et al (Yamamura, R. and Y. Shimomura (1997): *Industrial high-performance liquid chromatography purification of docosahexaenoic acid ethyl ester and docosapentaenoic acid ethyl ester from single cell oil*. JAOCS, 74(11), 1435-1440) report an HPLC production method starting from a single-cell oil in which the production costs were not reported. The DHAEE productivity was 0.1 kg/h. When the column used is considered (approximately 160 kg of silica gel), this gives a productivity of 0.0006 kg per kg of stationary phase per hour. This corresponds to a loading of 0.06%. The solvent used was toxic methanol.

It becomes clear that chromatographic systems encompass a multiplicity of problems for purifying PUFAs and are therefore unsuitable for producing polyunsaturated fatty acids on a relatively large scale (Zhou, Dequan and Xuebing Xu (2000): *Enzymatic enrichment of Long-chain Polyunsaturated Fatty Acids from Fish Oils*. Shipin Kexue (Bejing), 21(12), 188-194. Teramoto, M.; H. Matsuyama; N. Ohnishi; S. Uwagawa and K. Nakai (1994): *Extraction of ethyl and methyl esters of polyunsaturated fatty acids with aqueous silver nitrate solutions*. Ind. Eng. Chem. Res., 33, 341-345).

On the other hand, mild extraction methods could offer considerable advantages for obtaining PUFAs from mixtures with other substances.

First approaches toward such aqueous extraction systems containing silver nitrate have been investigated (Suzuki, T.; S. Kikuchi; K. Nakano; S. Kato and K. Nagahama (1993): *Supercritical fluid extraction of polyunsaturated fatty acid ethyl esters from aqueous silver nitrate solution*. Bioseparation, 3, 197-204, Teramoto et al 1994). Kato et al (S. Kato, N. Kunio, N. Hidetomi and N. Kaoru (1994): *Separation and recovery of polyunsaturated fatty acids by emulsion film method*. JP06279781) studied the use of oil-in-water emulsions, only separation of the overall PUFA fraction being reported. In this case, however, the use of silver nitrate, which is hazardous to health, is a hindrance for an industrial application. Furthermore, in an aqueous environment, a risk of oxidation of the PUFAs is particularly high, which can be further accelerated, in particular, by the presence of silver nitrate. The handling of silver nitrate additionally proves to be very difficult, since silver nitrate can be relatively rapidly oxidized to silver oxide and is generally considered unstable.

Solid-phase extraction systems without silver which have already been described do not show sufficient selectivity in the separation of PUFAs (Wilson, R.; J. R. Henderson; I. Burkow and J. R. Sargent (1993): *The enrichment of n-3 polyunsaturated fatty acids, using aminopropyl solid phase extraction columns*. Lipids, 28(1), 51-54). Solid-phase extraction processes using silver for separating PUFAs, in particular without using acetonitrile, are not known to the applicants.

In addition, purification by facilitated diffusions through silver-loaded membranes has been attempted [Shibaki, A.; Y. Irimoto; K. Saito; K. Sugita; T. Baba; I. Honjyo; , S. Moriyama and T. Sugo (1999): *Selective Binding of Docosahexaenoic acid ethyl ester to a silver ion-loaded porous hollow-fiber membrane*. JAOCS, 76(7), 771-775].

Owing to directive 88/344/EEC of Jun. 13, 1988 on the approximation of the laws of the Member States on extraction solvents, which must be heeded in the production of foodstuffs and food ingredients, when DHA is produced for the food sector, the use of acetonitrile must be absolutely excluded.

In view of said prior art, the object underlying the present invention was therefore to provide a novel method for obtaining unsaturated compounds from mixtures with other substances, for example other organic saturated or less highly unsaturated compounds.

This method should make possible a quantitatively sufficient purification which is better than is described in the prior art, and permit a simplification of the method and economical design of the same. Moreover, the method should be selective in order to permit, for example, the separation from one another of unsaturated compounds which differ only slightly structurally.

A further object of the present invention was to provide a novel method for obtaining unsaturated fatty acids or derivatives thereof from mixtures with other substances.

This method should make possible a quantitatively sufficient purification of PUFAs which is better than is described in the prior art, and permit a simplification of the method and economical design of the same. Moreover, the method should be selective in order, for example, to make it possible to separate unsaturated fatty acids or derivatives thereof differing structurally only slightly, for example DHAEE/DPAEE.

Preferably, the inventive method is to be suitable for use in the food sector, and therefore, for example, make it possible to purify PUFAs from mixtures without the use of acetonitrile or other toxic solvents as extraction media.

This object, and also other objects which are not mentioned explicitly but which can be derived as such or can be inferred from the contexts discussed at the outset herein, is achieved by a method as claimed in patent claim 1. Expedient modifications of the inventive method are claimed in the subclaims which are referred back to claim 1.

This is because the inventive object can be achieved astonishingly simply by (i) loading a strongly acidic cation exchanger with silver ions, (ii) mixing the loaded cation exchanger with a liquid mixture containing the unsaturated compound to be purified with or without at least one solvent, (iii) in a batch method, contacting the mixture with the exchanger for a certain time at a defined temperature which is below the boiling point of the solvent used, (v) separating off the supernatant, and (vi) detaching the unsaturated compound from the ion exchanger.

In contrast to the abovementioned methods, in the present application, in addition to the silver ions required for the separation, a matrix is used (ion exchanger) which makes a considerable contribution to the selectivity, reaction time and quality of the separation. Thus, in the methods described in the prior art, it can also be observed that, although silver ions are present, no separation of the PUFAs is achieved.

Depending on the number of double bonds and the field of application (food or drugs) and the solvents thereby approved, different procedures are followed in the present method. Thus, fatty acids which have fewer than 4 double bonds can in principle be detached quantitatively from the exchanger without acetonitrile. Fatty acids having more than 4 double bonds can only be quantitatively detached from the exchanger when acetonitrile (FIG. 1: variant A), the novel regeneration method (FIG. 1: variant B) or a partially silvered exchanger (FIG. 1: variant C) is used.

Generally, it can be observed that polyunsaturated fatty acids bind to the exchanger with different strengths. Thus, in some cases, quantitative detachment is observed even in a polar solvent with or without additional heating. This can be explained by the differing degree of complexation of the PUFA. Thus a triunsaturated PUFA can enter into a maximum of 6 complex bonds and a hexaunsaturated PUFA can enter into a maximum of 12 complex bonds, and thus form the stronger bonding species.

The unsaturated compound can be detached according to the invention from the cation exchanger at a temperature of from −20° C. to 80° C. Preferably, the unsaturated compound is detached at a temperature of from −20° C. to 40° C., very particularly preferably at from −20° C. to 10° C. The detachment can be performed according to the invention by adding a solvent selected from the group consisting of ketones (preferably acetone, 2-methyl ethyl ketone), medium-chain alcohols (preferably 2-propanol, propanol or butanol), short-chain alcohols (preferably methanol or ethanol) and nitriles (preferably acetonitrile).

Compounds which can be isolated according to the invention from mixtures comprise, inter alia, fatty acids (saturated, unsaturated or polyunsaturated), isomeric fatty acids (cis, trans, conjugated, isolated), fatty acid derivatives (e.g. ethers or esters, for example methyl ester, ethyl ester, wax esters, triglycerides, diglycerides, monoglycerides), modified fatty acids (for example hydroxy fatty acids, oxo fatty acids (keto ), amino fatty acids) also as derivatives, unsaturated alkenes, unsaturated alcohols, unsaturated ethers, unsaturated ketones or aldehydes, aromatics, steroids or steroid esters, sugars (monomers, oligomers, . . . ), tocopherols, astaxanthin.

Fatty acids which can be isolated according to the invention from mixtures with other organic compounds comprise, inter alia: hexadecadienoic acids, hexadecatrienoic acids, hexadecatetraenoic acids, linoleic acid, γ-linolenic acid, α-linolenic acid, stearidonic acid, arachidonic acid, eicosatrienoic acids, eicosatetraenoic acids, eicosapentaenoic acids, docosapentaenoic acids, docosahexaenoic acid, tetracosadienoic acids, octacosaoctaenoic acids and their salts or esters, ethers or other derivatives of these fatty acids.

Preferably, the fatty acid ethyl esters are purified by this method.

Generally, fatty acids which can be purified according to the invention are all fatty acids of the chain length C14-C30, or derivatives of such fatty acids, which have more than two double bonds.

Separation of compounds depending on the position of the double bonds or on the configuration of the double bonds is possible using the inventive method.

In principle, when fully silvered exchangers are used, the best selectivities and the highest loadings of the exchangers with PUFA are achieved.

According to the invention, the starting mixtures which can be used are natural oils, for example fish oils, vegetable oils, microbially produced oils, processed oils, ester mixtures, free fatty acid mixtures, unsaturated compounds and/or derivatives of such compounds.

Fish oils contain, for example, 10-20% DHA, and microbially produced oils contain up to 60% DHA. Therefore, the oils also contain differing amounts of fatty acids to be separated off. For a person skilled in the art, this gives the difficulty [lacuna] a specific purity of the pure DHA which is achievable by the purification step. Generally, therefore, it makes more sense to define a purification factor to assess the quality of the purification. The purification factor, in the simplest case, can be the quotient of the purity of the product and the purity of the substrate. The purities can be determined, for example, from gas-chromatographic analysis (unit: area %).

$$P_F = P_{fatty\ acid\ in\ the\ product} / P_{fatty\ acid\ in\ the\ substrate} * 100\%, \text{ where}$$

$P_F$=Purification factor (%)
$P$=Purity

The purification factors after a successful purification are always >1. However, depending on the starting mixture, even higher values can be achieved; in the case of a starting mixture which has the target fatty acid at 0.5% and, after purification, a purity of 95%, for example 190.

In the example of DHAEE, a high-purity 95% DHAEE can be produced not only from a 47% pure DHAEE mixture, but also from an 80% pure DHAEE mixture. The purification factors in these examples are between 1.19 and 2.02.

To carry out the inventive method, no chromatography column is required and no fractionation in the actual sense needs to be carried out.

Before the separation of supernatant and product phase, only a single equilibrium needs to be established. This is in complete contrast to chromatography (for example HPLC, SFC), in which a separation is only achieved after achieving a certain number of plates (for example column), or after establishing a very high number, in some circumstances, of equilibria.

Technical problems which usually occur owing to change of solvent in chromatography (air bubbles, swelling of the exchanger, inhomogeneities) do not occur in the inventive method. Likewise, flow problems (inhomogeneous flow) over the separation column (gradient formation) do not occur. At the same time, higher product purities can be achieved. It is also possible to set the product purity in a targeted manner.

Surprisingly, it has been shown by the abovementioned inventors that polyunsaturated fatty acids or derivatives of these polyunsaturated fatty acids (for example DHAEE) can be complexed in one step from a solution (e.g. DHAEE/DPAEE) in a batch process in a highly selective manner on a silver-loaded cation exchanger.

The selectivity of the complexation may surprisingly be controlled very simply, depending on the fatty acid concentration to be separated, the type of ion exchanger used and its amount, the solvent used, the temperature, the time and the silver loading of the ion exchanger.

These relationships can be used in a targeted manner for the purification. By establishing certain conditions, high-purity PUFAs can be produced without complex chromatography steps.

The novel method is therefore not a chromatography method, but a selective extraction method (complexing more highly unsaturated fatty acids/derivatives on the cation exchanger or cation exchangers and a subsequent decomplexation step in a simple stirred vessel in a batch method).

Cation exchangers which can-be used according to the invention may be found in the following list, with the usual trade. names being cited: Dowex® 50 WX8, Dowex® 50 WX4, Dowex® 50 WX2, Dowex® MWC1, Dowex® MSC1, Dowex® Monosphere C-350, Dowex® CCR-2, Dowex® DR 2030, Amberlite® CG50, Amberlite® IR-120, Amberlyst® 15, Bio-Rex® 70 Resin, Macherey & Nagel PS-DVB®. In particular, those cation exchangers which have the following properties can be used:

Strongly acidic cation exchangers: gels which have as parent substance styrene with divinylbenzene branches, have sulfonic acid and/or carboxyl groups as active silver-bearing group and are microporous, or are preferably macroporous. In particular, macroreticular ion exchangers are also particularly suitable, since they are solvent-stable and have a considerably larger surface area compared with gels. These likewise bear sulfonic acid and/or carboxyl groups as functional groups.

Amberlyst® 15 and Dowex® DR2030 can be used with particular preference.

The loading capacity of the cation exchangers usable according to the invention ranges in this case from 0.1 to 15% by weight (g of PUFA/100 g of H$^+$ exchanger) of total PUFA.

This novel method represents, in a surprisingly simple manner, a great simplification and economical enhancement of the purification processes described to date in the prior art. Also, it is possible without any problems to adapt this method to large-scale and industrial purposes, since, for example, columns etc. are not used.

Also, it was completely surprising to observe that the purity of the product on the cation exchanger can be markedly increased and selectively controlled by a subsequent washing operation with a solvent and subsequent heating in one or more solvents.

The heat supply can be provided, according to the invention, for example, by using external heat sources, by electromagnetic radiation, for example microwaves or infrared radiation, or else via ultrasound treatment. Any heat sources that are beneficial to the process can be used.

It is suspected here that, owing to the effect of heat (energy), incompletely complexed fatty acid in which not all double bonding electrons are present in complexed form (this can be the product fatty acid, but also secondary fatty acids or derivatives) is decomplexed, preferably the more highly unsaturated fatty acid, after decomplexing, being recomplexed to the cation exchanger and occupying the positions which have become free there. The secondary fatty acid, which is likewise decomplexed, is, according to this theory, thus reattached only to a subsidiary extent to the silver-loaded cation exchanger and the majority remains in the supernatant. The purity of the product fatty acid on the cation exchanger is considerably increased as a result.

According to the invention, therefore, heat can be supplied to the system after complexing the fatty acid to the 100% silver-loaded cation exchanger, in order to ensure greater purity of the fatty acid. Preferably, this step is carried out at a temperature T>40° C. and a pressure P=1 bar. Particularly preferably the step is carried out between 40° C. and 80° C. Very particularly preferably between 50 and 70° C., and very particularly preferably at from 55° C. to 65° C.

If temperatures of >40° C. are employed, the duration of the complexation reaction can be incremented in 30-minute steps, quite generally longer reaction times giving a higher product purity. However, it has been found that 2.5 h should be sufficient in most cases.

The use of acetonitrile as decomplexing agent can be omitted completely in the inventive method in the case of PUFA or PUFA derivatives having fewer than 4 double bonds, since conditions have been developed in which (i) the detachment succeeds in physiologically safe solvents and (ii) a completely novel regeneration method has been developed for the cation exchanger or the silver itself.

A solvent which can be used according to the invention for the attachment of the PUFA or of the derivative can be selected from the following groups: alkanes, ketones, ethers, esters, diketones, diesters, diethers, diols, polyols, nitrites, dinitriles and alcohols; particularly suitable ketones are acetone and 2-methyl ethyl ketone [sic], particularly suitable alcohols are the medium-chain alcohols 2-propanol, propanol, butanol, hexanol or isomers thereof, still more suitable are the alkanes n-hexane, n-heptane, n-octane or isomers thereof, and most suitable is the nitrile acetonitrile, and also the short-chain alcohols ethanol and methanol. Ethanol and methanol are the preferred solvents.

According to the invention, the silver can, after each step of attaching fatty acids to the ion exchanger, be detached by adding an acid (e.g HNO$_3$) or base (e.g. NaHCO$_3$). The complexed fatty acid is thus released at the same time. The silver precipitates out as salt (e.g. Ag$_2$CO$_3$) or remains in solution (AgNO$_3$) and can be separated off from the product fatty acid by decanting or extraction.

The silver can then be brought back into solution according to the invention by adding a base (in the case of a preceding detachment by HNO$_3$, for example by adding NaHCO$_3$) or an acid (in the case of a preceding detachment by NaHCO$_3$, for example by adding HNO$_3$).

The following bases, inter alia, can be used according to the invention: hydroxides and carbonates, organic bases, in particular sodium hydroxide, potassium hydroxide, preferably triethylamine, calcium carbonate, magnesium carbonate, very particularly preferably potassium carbonate, potassium hydrogen carbonate, sodium carbonate and sodium hydrogen carbonate.

The following acids, inter alia, can be used according to, the invention: phosphoric acid, in particular hydrochloric acid, formic acid and sulfuric acid, very particularly preferably acetic acid and nitric acid.

As a result of the higher affinity of most ion-exchanger materials toward Ag$^+$ compared with other cations (Ag$^+$ >>Na$^+$>>H$^+$), the silver is attached quantitatively to the cation exchanger. After various washing steps, the cation exchanger is reusable. The reattachment of the silver is then at least 90%, preferably at least 95%, and very particularly preferably >99%, compared with the first attachment.

Using the inventive method, purification factors of from 1.01 to 99 can be achieved, in which case, although these purification factors do depend on the method, they also depend on the concentration of the target compound in the starting mixture. Although therefore high purification factors are expedient, it can nevertheless be of great importance to bring, for example, a target fatty acid from 80% purity to 90%, precisely when, as shown in the examples, molecules are separated from one another which only differ from one another in the presence of a single further double bond. Although the corresponding purification factor in this example is "only" 1.125, in conjunction with the high inventive yields, this means a dramatic further development of all methods and processes described in the prior art, for example chromatographic methods and processes.

In the inventive method, in the case of PUFAs or PUFA derivatives containing 4 or more double bonds, a fully silvered cation exchanger can be used, from which the PUFAs are successfully detached using acetonitrile, or else by regeneration of the cation exchanger or of the $Ag^+$, as described previously.

However, according to the invention, for PUFAs or PUFA derivatives having 4 or more double bonds, preferably a partially silvered cation exchanger can also be used, the detachment in this case being able to be performed by physiologically harmless solvents and/or heat, without the use of acetonitrile.

A solvent which can be used according to the invention for detaching the PUFA or the derivative can be selected from the following groups: ketones (for example acetone, 2-methyl ethyl ketone [sic]), preferably medium-chain alcohols (for example 2-propanol, butanol, propanol), very particularly preferably short-chain alcohols (for example methanol or ethanol) or mixtures of these solvents.

The invention relates to a method for fractionating a liquid mixture according to the degree of saturation of the compounds present in the mixture. The degree of saturation depends on the number of double bonds. The mixture can contain polyunsaturated organic compounds, unsaturated organic compounds, or else saturated organic compounds and also inorganic compounds.

Figure 2:
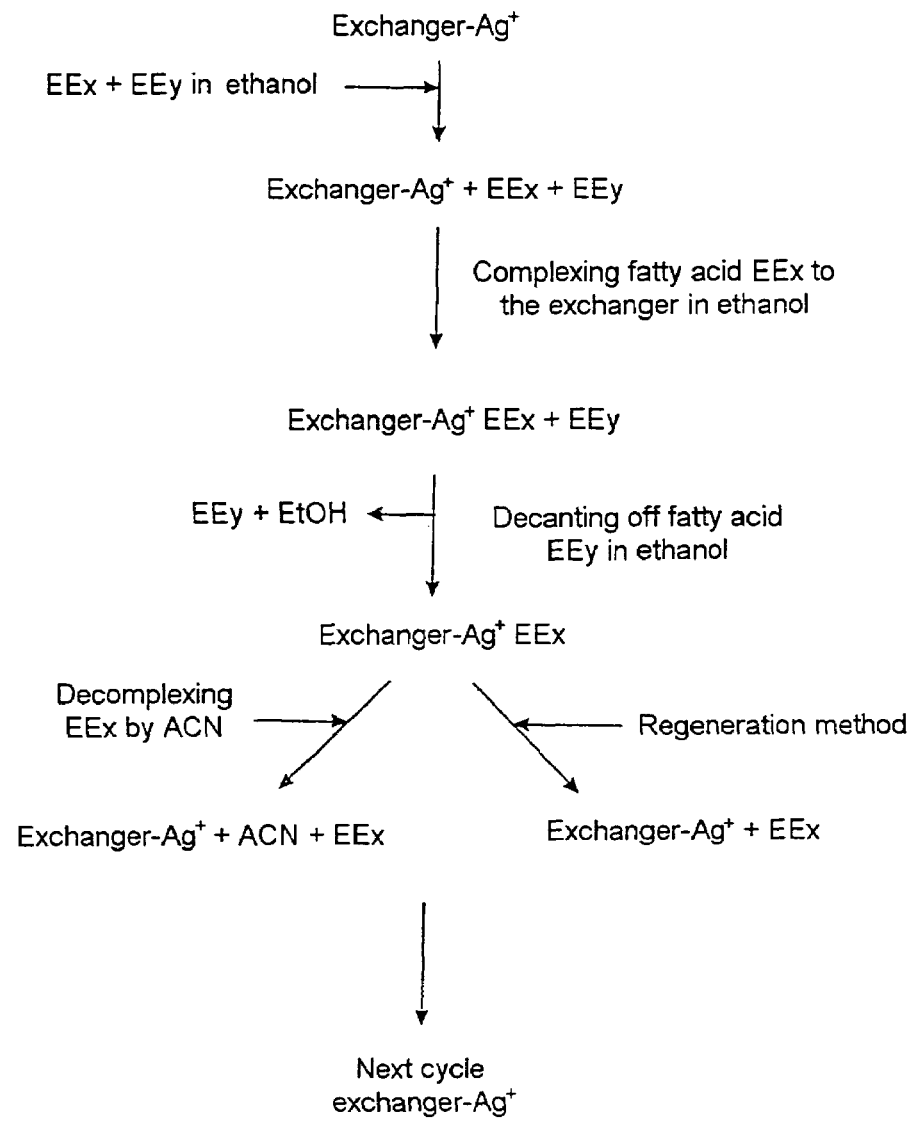
Figure 3:
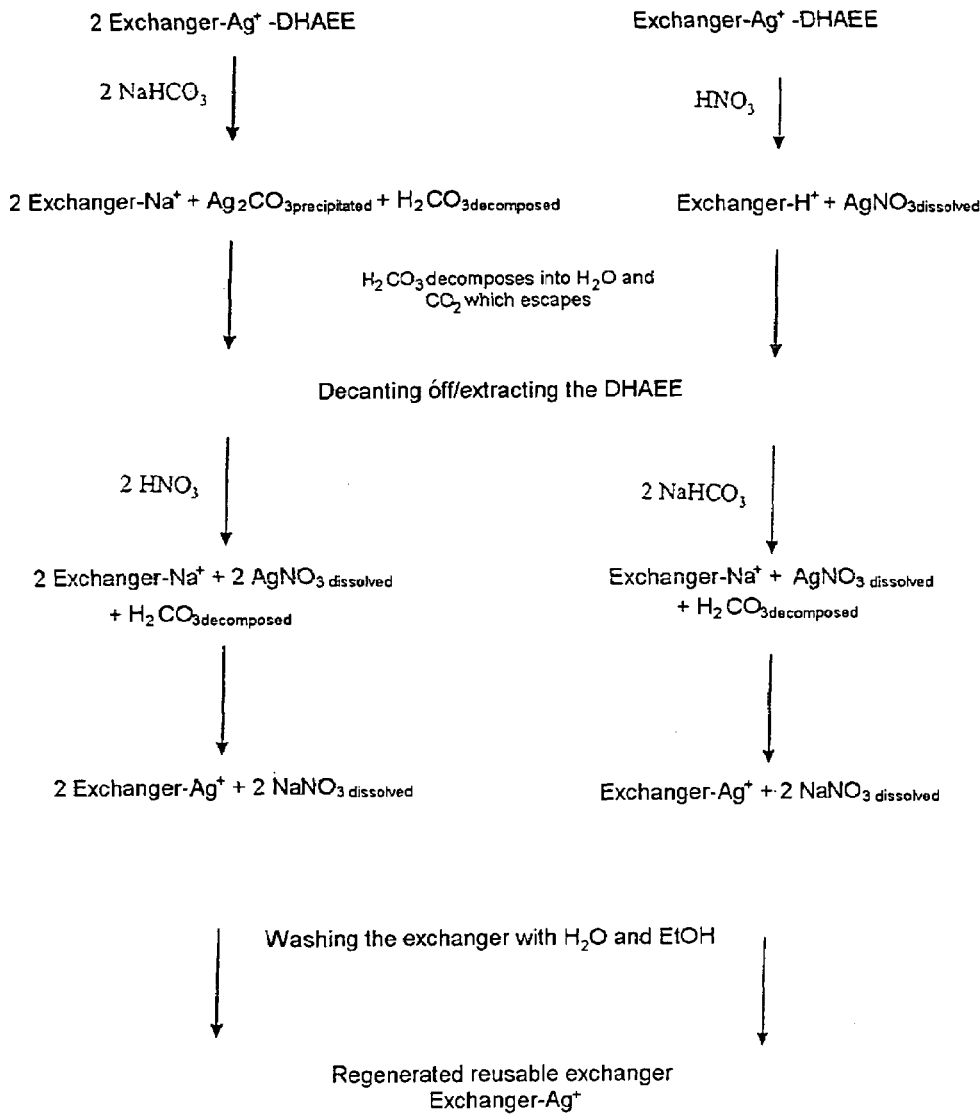

THE FIGURES BELOW EXPLAIN THE INVENTION IN MORE DETAIL:

FIG. 1 shows the principle of purifying PUFAs by selective extraction from the $Ag^+$ ion exchanger according to the solvent which can be used FIG. 2 shows a plan of the inventive complexation of fatty acid ethyl esters on the $Ag^+$ ion exchanger FIG. 3 shows a plan of the inventive regeneration of the silver

ABBREVIATIONS USED:

DHA All cis-4,7,10,13,16,19-docosahexaenoic acid
DPA All cis-4,7,10,13,16-docosapentaenoic acid (ω-6)
DHAEE All cis-4,7,10,13,16,19-docosahexaenoic acid ethyl ester
DPAEE All cis-4,7,10,13,16-docosapentaenoic acid ethyl ester (ω-6)
SFC Supercritical fluid chromatography
PUFA Polyunsaturated fatty acid Terms Used:

Loading Capacity

The loading capacity of the cation exchanger describes the amount of PUFA or defined derivative (for example docosahexaenoic acid ethyl ester; DHAEE) in g or percent (%, w/w) which can be complexed to 100 g of the cation exchanger in the protonated form ($H^+$ form).

The invention will be illustrated with reference to the following examples, without these being able to be considered as a limitation of the invention.

Unless stated otherwise, in all of the following examples the substrate used for the purification was a mixture of about 80% DHAEE and 20% DPAEE (ω-6), which can be obtained from a microbial fermentation using the strain Schizochytrium SR21 [Yokochi et al., Optimization of docosahexaenoic acid production by *Schizochytrium limacinum* SR21", Appl. Microbiol. Biotechnol. (1998), 49: 72-76]. The Schizochytrium oil obtained from this fermentation was transesterified into the ethyl esters and subjected to precipitation with urea, the saturated fatty acids being removed. DHAEE and DPAEE can be further purified by means of HPLC [Yamamura, supra], and used as substrate for the purification experiments. Separation of the ethyl esters from one another in quantitatively significant amounts is a great problem, since the two fatty acids differ only in the differing number of double bonds.

EXAMPLE 1

Production of Amberlyst®15 (20-50 Mesh) 100% Loaded with Silver Ions

The silver-loaded ion exchangers are produced on the basis of the method described by Nieto et al. (Nieto, S.; A. M. Cordoba; J. Sanhuenzy and A. Valenzuela (1997): *Obtention of highly purified fractions of eicosapentaenoic acid and docosahexaenoic acid from sardine oil by silver-resin chromatography*: A semipreparative procedure. Grasas y Aceites, 48(4), 197-199) for Dowex® 50WX8 (earlier name Dowex® W-HCR-W2). However, the method for this was considerably simplified and modified.

Neither is the material prepared in a heatable glass column, nor is the material prewashed with organic solvents. However, in the inventive novel method, in contrast to the method disclosed by Nieto et al., the particle size of the material is be [sic] decisive for the quality of the separation and yield.

20 g of Amberlyst® 15 are placed in a vacuum filter or glass column equipped with a vacuum filter and washed with 1 M sodium nitrate solution ($NaNO_3$) until the pH of the eluate turns from acidic to neutral. Neutralization indicates reduced formation of nitric acid which is formed on exchange of protons to release sodium ions. If the cation exchanger is completely loaded with sodium ions, the eluent remains neutral.

Two different procedures can then be followed.

Either the sodium-loaded cation exchanger is washed with 0.4 M silver nitrate solution until silver can be detected in the eluent, or the material is first transferred by rinsing with sodium nitrate solution into a round-bottomed flask or conical flask. The excess sodium nitrate solution is then discarded.

Subsequently, 5.4 ml of 0.4 M silver nitrate solution/g of Amberlyst® 15 are stirred for 8-12 h. The supernatant is removed.

In both cases the procedure with the $Ag^+$-loaded cation exchanger is as follows:

The silver-loaded cation exchanger (approximately 2.0 mmol of $Ag^+$/ml of $H^+$ exchanger, where 1 g of $H^+$ Dowex is equivalent to approximately 0.9 ml of $H^+$ Dowex) is washed to be silver free, three times with 100 ml of water, and then washed to be water free twice with 100 ml of ethanol (1 h). It is then left overnight (12 h) in 100 ml of acetonitrile. The material is then washed again twice, each time with 100 ml of ethanol. The material can then be used. Acetonitrile can also be replaced by using 100 ml of ethanol three times.

A different washing procedure or activation procedure can lead to less active or nonactive silver-loaded cation exchanger. The water content in the silver-loaded cation exchanger is of particular importance here.

EXAMPLE 2

Production of Amberlyst® 15 (20-50 Mesh) Ion Exchanger which is Partially Loaded, to 50%, with Silver Ions Partially silvered Amberlyst® material is prepared with stirring in order to enable a uniform distribution of the silver on the cation exchanger.

50% silvered Amberlyst® 15 material is prepared by adding 2.7 ml of 0.4 M silver nitrate solution/g of Amberlyst® 15 for 8-12 h. The batch will be stirred for 12 h. The supernatant is then decanted and the silver-loaded cation exchanger is washed three times using twice-distilled water. The material is then washed twice with 100 ml of ethanol (1 h each time) and washed once with 100 ml of acetonitrile (12 h). The acetonitrile can be replaced by multiple use of ethanol. The material is finally taken up in ethanol and then used.

In the same way, material of 0.1-99.9% (based on 100% silvering) silvering can be prepared.

Various Detachment Protocols (FIG. 1)

Variant A. Detaching the Products from the $Ag^+$ Exchanger Using a π-Electron Donor The solvent which can detach the product ester from the silver-loaded cation exchanger must be chosen depending on the exchanger material, silver loading and the attached fatty acid ethyl ester (number of double bonds). In the ideal case, a solvent can be used which likewise acts as π-electron donor. Examples of this are acetonitrile, 1-hexene or toluene.

For example, bound DHAEE can be separated off from the silver-loaded cation exchanger in the most simple manner by adding acetonitrile (ACN). The acetonitrile in this case is a stronger π-electron donor than the PUFAs.

For this, 100 ml of ACN are added to the batch and the mixture is stirred at room temperature under a protective gas. After complete detachment of the fatty acid ethyl ester, the organic phase is taken off. The exchanger material is washed again with ACN and the organic phases are combined. After taking off the solvent, the purified DHAEE is obtained as a slightly yellow oil. In all of the examples listed, just relatively small amounts of acetonitrile are sufficient for this, for example a mixture of acetonitrile in n-hexane (10:90, v:v).

Examples 3-9 below are examples of such methods in which ACN is used to detach the complexed fatty acid from the exchanger.

EXAMPLE 3

Experimental Attachment of a Mixture of DHAEE and DPAEE to $Ag^+$ Amberlyst® 15 (20-50 Mesh) in Ethanol over 24 Hours:

In preliminary experiments it was found that the PUFA loading capacity of the exchanger is approximately 5% by weight of PUFA (g of PUFA/100 g of $H^+$ exchanger).

597.8 mg of docosahexaenoic acid ethyl ester (DHAEE) and 144.0 mg of docosapentaenoic acid ethyl ester (ω-6 DPAEE) were added to a stirred solution of the 100% silver-loaded exchanger (10 g of $H^+$ Amberlyst® 15) from example 1 in 100 ml of absolute ethanol. The suspension is shaken at 100 rpm for 24 h at room temperature under a protective gas. An antioxidant may be further added (e.g. tocopherols, 2,6-di-tert-butyl-4-methylphenol (BHT), ascorbyl palmitate) to avoid oxidation of the PUFAs.

After time intervals of 30 or 60 min in each case, the reaction is assessed quantitatively and qualitatively by analyzing the supernatant by gas chromatography (HPGC6890, column: Macherey & Nagel FFAP Permabond 0.1 μm (25 m, 0.25 mm), with splitting (10:1), carrier gas: helium (constant flow 1.0 ml/min), FID operation using hydrogen (30 ml/min) and oxygen (300 ml/min) as fuel gases, make up: 20 ml of helium, detector and injector temperatures: in each case 255° C., GC furnace temperature program: initial temperature 180° C., temperature rise rate 10° C./min to a final temperature of 230° C., hold this for 5 min, injection volume: 1.0 μl). By adding to the reaction batch an internal standard which does not bind to the silver-loaded cation exchanger (for example a saturated fatty acid or an ester of a saturated fatty acid, or another derivative), quantitative analysis of the polyunsaturated fatty acids in the supernatant can be carried out.

The theoretical loading of the exchanger can be calculated in this case by subtracting the fatty acid ethyl ester remaining in the supernatant from the total fatty acid ethyl ester used. The purity of the product can likewise be determined in this way (table 1).

In this case, virtually all of the DHAEE (86.7%) was complexed on the exchanger. The purity of the DHAEE was increased from 80% to virtually 91%. The complexation is complete after only a few hours.

When the ion exchanger is completely loaded with PUFAs (further attachment no longer observable) or the desired purity (e.g. DHAEE >90%) is achieved, the supernatant is taken off, and the ion exchanger material is washed once with 100 ml of ethanol and freed from residues of unbound fatty acid ethyl ester. After the reaction is complete, the bound product fatty acid ethyl ester can be detached from the silver-loaded cation exchanger by various methods.

Most simply, DHAEE can be detached by stirring with 100 ml of acetonitrile for 7 h under a protective gas. For this, simply a 10% strength mixture of acetonitrile in ethanol or n-hexane is sufficient. After removing the solvents, 482.6 mg of the purified DHAEE were isolated at a purity of 88.4%.

This value agrees well with the calculated value from table 1. The yield of DHAEE is 81%. The product loading of the exchanger is thus 4.8% (g of DHAEE/100 g of $H^+$ exchanger).

From the supernatant, after removing the solvents, a further 66.4 mg of DHAEE were isolated. The overall DHAEE recovery was 92%.

TABLE 1

Results of attaching a mixture of DHAEE and DPAEE to Ag⁺ Amberlyst ® 15

| Time (h) | S DPAEE (area %) | S DHAEE (area %) | S DPAEE (mg) | S DHAEE (mg) | Total (mg) | R in EtOH (%) | DHAEE Amberlyst (mg) | DPAEE Amberlyst (mg) | DHAEE Amberlyst (area %) | DHAEE yield Amberlyst (%) | Purification factor DHAEE |
|---|---|---|---|---|---|---|---|---|---|---|---|
| 0 | 20.5 | 79.5 | 146.6 | 567.7 | 714.3 | 96.3 | 30.1 | −2.5 | 109.2 | 5.0 | |
| 1 | 39.0 | 61.0 | 100.7 | 158.3 | 259.0 | 34.9 | 439.4 | 43.3 | 91.0 | 73.5 | 1.14 |
| 2 | 45.0 | 55.0 | 99.0 | 121.4 | 220.4 | 29.7 | 476.4 | 45.0 | 91.4 | 79.7 | 1.14 |
| 3 | 46.4 | 53.6 | 100.8 | 116.6 | 217.4 | 29.3 | 481.2 | 43.3 | 91.8 | 80.5 | 1.15 |
| 7 | 50.8 | 49.2 | 96.8 | 94.0 | 190.8 | 25.7 | 503.8 | 47.2 | 91.4 | 84.3 | 1.14 |
| 24 | 53.6 | 46.4 | 91.8 | 79.4 | 171.2 | 23.1 | 518.4 | 52.2 | 90.8 | 86.7 | 1.14 |

S: supernatant,
R = recovery,
Amberlyst ® 15

EXAMPLE 4

Experimental Attachment of a Mixture of DHAEE and DPAEE to Ag⁺ Amberlyst® 15 (20-50 Mesh) in Ethanol over 210 Minutes For this, a mixture of 0.585 g of docosahexaenoic acid ethyl ester (DHAEE) and 0.146 g of docosapentaenoic acid ethyl ester (ω-6 DPAEE) is added to a stirred solution of the 100% silver-coated exchanger (equivalent to 10 g of H⁺ Amberlyst® 15) in 100 ml of absolute ethanol. The suspension is shaken at 100 rpm for 210 min at 26° C. under a protective gas. At the times indicated, the supernatant was analyzed by gas chromatography.

The purity and yield of the product can likewise be determined in this manner (table 2).

Compared with the experimental attachment using Dowex® 50WX8 200-400 mesh (example 6, table 4), a considerably reduced reaction time and a marked increase of the DHAEE loading from 1.2% (g of DHAEE/100 g of H⁺ Dowex 50WX8) to 4.6% (g of DHAEE/100 g of H⁺ Amberlyst®) was observed. The purity of the DHAEE was increased from 80% to over 92.9%. The yield of 92.9% pure DHAEE is 77.9%. The comparable exchanger (particle size) from the Dowex® 50WX8 series (20-40 mesh) does not show any DHAEE loading capacity and, therefore, also no purifying effect.

EXAMPLE 5

Experimental Attachment of a Mixture of DHAEE and DPAEE to Ag⁺ Amberlyst® 15 (20-50 Mesh) in n-hexane:

For this, 585.1 mg of docosahexaenoic acid ethyl ester (DHAEE) and 146.0 mg of docosapentaenoic acid ethyl ester (ω-6 DPAEE) are added to a stirred solution of the completely silver-loaded exchanger (9.3 g of H⁺ Amberlyst® 15) in 100 ml of n-hexane. The suspension is shaken at 100 rpm for 3.5 h at room temperature under a protective gas.

After time intervals of 30 or 60 min in each case, the reaction is assessed quantitatively and qualitatively by analyzing the supernatant by gas chromatography. The theoretical loading of the exchanger can be calculated here by subtraction. The purity of the product can likewise be determined in such a manner (table 3).

The purity of the DHAEE was increased 80% to over 94.5%. The addition is virtually complete after only a few minutes. The loading of the exchanger with DHAEE is 4.4% of DHAEE/100 g of H⁺ exchanger). The yield of 94.5% pure DHAEE is 74.6%.

The supernatant is taken off, the cation exchanger material is washed once with 100 ml of n-hexane and freed from residues of unbound fatty acid ethyl ester. After the reaction

TABLE 2

Results of attaching a mixture of DHAEE and DPAEE to Ag⁺ Amberlyst ® 15 (20-50 mesh)

| Time (min) | S DPAEE (area %) | S DHAEE (area %) | S DPAEE (mg) | S DHAEE (mg) | Total (mg) | R in EtOH (%) | DHAEE Amberlyst (mg) | DPAEE Amberlyst (mg) | DHAEE Amberlyst (area %) | DHAEE yield (%) | Purification factor DHAEE |
|---|---|---|---|---|---|---|---|---|---|---|---|
| 0 | 20.6 | 79.4 | 180.9 | 696.4 | 877.3 | 120.0 | −111.4 | −34.9 | 76.1 | −19.0 | |
| 10 | 25.6 | 74.4 | 130.7 | 380.2 | 510.9 | 69.9 | 205.0 | 15.3 | 93.0 | 35.0 | 1.16 |
| 20 | 29.1 | 70.9 | 119.2 | 290.3 | 409.5 | 56.0 | 294.8 | 26.8 | 91.7 | 50.4 | 1.15 |
| 30 | 32.3 | 67.7 | 118.8 | 248.8 | 367.5 | 50.3 | 336.3 | 27.2 | 92.5 | 57.5 | 1.16 |
| 45 | 35.5 | 64.5 | 117.1 | 212.2 | 329.3 | 45.0 | 372.9 | 28.9 | 92.8 | 63.7 | 1.16 |
| 60 | 37.3 | 61.2 | 117.3 | 192.5 | 309.7 | 42.4 | 392.7 | 28.7 | 93.2 | 67.1 | 1.17 |
| 150 | 44.2 | 55.8 | 114.4 | 144.5 | 258.9 | 35.4 | 440.6 | 31.6 | 93.3 | 75.3 | 1.17 |
| 210 | 43.9 | 51.0 | 111.4 | 129.5 | 240.8 | 32.9 | 455.7 | 34.7 | 92.9 | 77.9 | 1.16 |

S: supernatant,
T: silver-loaded cation exchanger,
R = recovery is complete, the bound product fatty acid ethyl ester can be detached from the silver-loaded cation exchanger by various methods.

Most simply, DHAEE can be detached by stirring with 100 ml of acetonitrile for 7 h under a protective gas. Instead of the pure acetonitrile, however, just a 10% strength mixture of acetonitrile in n-hexane can also be used, which achieves an identical result.

of the exchanger can be calculated by subtraction here. The purity of the product can likewise be determined in this manner (table 4).

The purity of the DHAEE was increased from 79% to 97.9%. The attachment is complete after only a few minutes. The loading of the exchanger with DHAEE is 5.5% (g of DHAEE/100 g of H$^+$ exchanger). The DHAEE yield is 47.1%.

TABLE 3

Results of attaching a mixture of DHAEE and DPAEE to Ag$^+$ Amberlyst ® 15

| Time (min) | S DPAEE (area %) | S DHAEE (area %) | S DPAEE (mg) | S DHAEE (mg) | Total (mg) | R in EtOH (%) | DHAEE Amberlyst (mg) | DPAEE Amberlyst (mg) | DHAEE Amberlyst (area %) | DHAEE yield (%) | Purification factor DHAEE |
|---|---|---|---|---|---|---|---|---|---|---|---|
| 0 | 20.7 | 79.3 | 158.8 | 609.1 | 767.9 | 105.0 | −24.0 | −12.7 | 65.3 | −4.1 | |
| 10 | 29.0 | 71.0 | 118.2 | 290.1 | 408.3 | 55.8 | 295.1 | 27.9 | 91.4 | 50.4 | 1.14 |
| 20 | 32.9 | 67.1 | 127.5 | 260.5 | 388.0 | 53.1 | 324.6 | 18.5 | 94.6 | 55.5 | 1.18 |
| 45 | 37.6 | 62.4 | 121.7 | 202.3 | 324 | 44.3 | 382.9 | 24.3 | 94.0 | 65.4 | 1.18 |
| 60 | 39.1 | 60.9 | 123.4 | 192.5 | 315.9 | 43.2 | 392.7 | 22.6 | 94.6 | 67.1 | 1.18 |
| 150 | 43.2 | 56.8 | 121.9 | 160.4 | 282.3 | 38.6 | 424.8 | 24.1 | 94.6 | 72.6 | 1.18 |
| 210 | 44.9 | 55.1 | 120.7 | 148.4 | 269.1 | 36.8 | 436.8 | 25.3 | 94.5 | 74.6 | 1.18 |

S: supernatant,
R = recovery,
Amberlyst: Amberlyst ® 15

TABLE 4

Results of attaching a mixture of DHAEE and DPAEE to Ag$^+$ Amberlyst ® 15 at 55° C.

| Time (min) | S DPAEE (area %) | S DHAEE (area %) | S DPAEE (mg) | S DHAEE (mg) | Total (mg) | R in n-hexane (%) | DHAEE Amberlyst (mg) | DPAEE Amberlyst (mg) | DHAEE Amberlyst (area %) | DHAEE yield (%) | Purification factor DHAEE |
|---|---|---|---|---|---|---|---|---|---|---|---|
| 0 | 20.5 | 78.9 | 312.7 | 1205.6 | 1518.3 | 103.0 | −25.9 | −18.4 | 58.6 | −2.2 | |
| 10 | 25.8 | 73.5 | 300.2 | 855.7 | 1155.9 | 78.4 | 324.1 | −5.8 | 101.8 | 27.5 | 1.27 |
| 20 | 27.1 | 72.9 | 288.0 | 775.2 | 1063.2 | 72.1 | 404.5 | 6.4 | 98.4 | 34.3 | 1.23 |
| 30 | 27.8 | 72.2 | 283.5 | 736.7 | 1020.2 | 69.2 | 443.0 | 10.9 | 97.6 | 37.6 | 1.22 |
| 45 | 28.6 | 71.4 | 292.9 | 731.6 | 1024.4 | 69.5 | 448.2 | 1.5 | 99.7 | 38.0 | 1.25 |
| 60 | 29.5 | 70.5 | 290.5 | 693.7 | 984.2 | 66.8 | 486.0 | 3.9 | 99.2 | 41.2 | 1.24 |
| 120 | 30.9 | 68.3 | 282.6 | 623.9 | 906.5 | 61.5 | 555.8 | 11.8 | 97.9 | 47.1 | 1.22 |

S: supernatant,
R = recovery,
Amberlyst: Amberlyst ® 15

EXAMPLE 6

Experimental Attachment of a Mixture of DHAEE and DPAEE to Ag$^+$ Amberlyst® 15 in n-hexane at Elevated Temperature:

For this, 1.18 g of docosahexaenoic acid ethyl ester (DHAEE) and 0.29 g of docosapentaenoic acid ethyl ester (ω-6 DPAEE) are added to a stirred solution of the completely silver-loaded exchanger (9.3 g of H$^+$ Amberlyst®) in 100 ml of n-hexane. The suspension is shaken at 100 rpm at room temperature [sic] under a protective gas for 2 h at 55° C. If appropriate, an antioxidant can further be added (e.g. tocopherol, ascorbyl palmitate), to prevent oxidation of the PUFAs.

After 30 or 60 min time intervals in each case, the reaction is assessed quantitatively and qualitatively by analyzing the supernatant by gas chromatography. The theoretical loading

EXAMPLE 7

Experimental Attachment of a Mixture of DHAEE and DPAEE to Ag$^+$ Dowex® 50WX8 (200-400) Mesh [sic]:

A study was also conducted to establish what influence the mesh size of the exchanger material used has on the separation.

For this, 291.4 mg of docosahexaenoic acid ethyl ester (DHAEE) and 72.7 mg of docosapentaenoic acid ethyl ester (ω-6 DPAEE) are added to a stirred solution of the completely silver-loaded exchanger (21 g of H$^+$ Dowex® 50WX8, 200-400 mesh) in 100 ml of absolute ethanol. The suspension is stirred at room temperature under a protective gas for 24 h at 300 rpm using a magnetic stirrer.

After 30 or 60 min time intervals in each case, the reaction is assessed quantitatively and qualitatively by analyzing the supernatant by gas chromatography. The theoretical loading of the exchanger can be calculated by subtraction here. The purity of the product can likewise be determined in such a manner (table 5).

The purity of the DHAEE was increased from 80% to 91.7%. The attachment is complete after 46 hours. The loading of the exchanger with DHAEE is 1.2% (g of DHAEE/100 g of H$^+$ exchanger). The yield of the 91.7% pure DHAEE is 83.7%.

In contrast to this, the DHAEE loadings with the fully silvered Dowex® 50WX8 100-200 mesh material are 1.1% (g of DHAEE/100 g of H$^+$ exchanger) and with the fully silvered Dowex® 50WX8 20-40 mesh material are virtually 0% DHAEE/H$^+$ exchanger. Here, therefore, a pronounced dependence on the particle size of the exchanger material is found.

(ω-6 DPAEE) are added to a stirred solution of the completely silver-loaded exchanger (25 g of H$^+$ Dowex® 50WX8, 100-200 mesh) in 200 ml of absolute ethanol. The suspension is stirred at room temperature under a protective gas for 24 h at 300 rpm using a magnetic stirrer. If appropriate, an antioxidant can further be added (e.g. tocopherol, ascorbyl palmitate), to prevent oxidation of the PUFAs.

After 30 or 60 min time intervals in each case, the reaction is assessed quantitatively and qualitatively by analyzing the supernatant by gas chromatography. The theoretical loading of the exchanger can be calculated here by subtraction. The purity of the product can likewise be determined in such a manner (table 6).

The purity of the DHAEE was increased from 80% to more than 92.8%. The attachment is complete after 24 hours.

TABLE 5

Results of attaching a mixture of DHAEE and DPAEE to Ag$^+$ Dowex ® 50 WX8 (200-400 mesh)

| Time (h) | S DPAEE (area %) | S DHAEE (area %) | S DPAEE (mg) | S DHAEE (mg) | Total (mg) | R in EtOH (%) | DHAEE Dowex (mg) | DPAEE Dowex (mg) | DHAEE Dowex (area %) | DHAEE yield (%) | Purification factor DHAEE |
|---|---|---|---|---|---|---|---|---|---|---|---|
| 0 | 17.7 | 73.2 | 66.9 | 277.6 | 344.5 | 94.6 | 13.8 | 5.7 | 70.6 | 4.8 | |
| 1 | 19.6 | 68.8 | 65.9 | 229.0 | 294.8 | 81.0 | 62.4 | 6.8 | 90.1 | 21.4 | 1.13 |
| 2 | 21.1 | 68.5 | 66.9 | 216.0 | 283.0 | 77.7 | 75.4 | 5.7 | 92.9 | 25.9 | 1.16 |
| 3 | 21.7 | 66.0 | 65.9 | 199.8 | 265.7 | 73.0 | 91.6 | 6.8 | 93.1 | 31.4 | 1.16 |
| 5 | 23.3 | 63.7 | 63.7 | 175.0 | 238.7 | 65.5 | 116.4 | 9.0 | 92.8 | 40.0 | 1.16 |
| 6.25 | 24.2 | 62.3 | 63.7 | 163.1 | 226.8 | 62.3 | 128.3 | 9.0 | 93.4 | 44.0 | 1.17 |
| 7 | 24.7 | 61.6 | 63.7 | 157.7 | 221.4 | 60.8 | 133.7 | 9.0 | 93.7 | 45.9 | 1.17 |
| 22 | 31.7 | 50.4 | 57.2 | 91.9 | 149.0 | 40.9 | 199.6 | 15.4 | 92.8 | 68.5 | 1.16 |
| 28 | 34.7 | 46.8 | 55.1 | 74.5 | 129.6 | 35.6 | 216.9 | 17.5 | 92.5 | 74.4 | 1.16 |
| 46 | 41.1 | 38.7 | 50.8 | 47.5 | 98.3 | 27.0 | 243.9 | 21.9 | 91.7 | 83.7 | 1.15 |

S: supernatant,
R = recovery,
Dowex: Dowex ® [lacuna] WX8

EXAMPLE 8

Experimental Attachment of a Mixture of DHAEE and DPAEE to Ag$^+$ Dowex® 50WX8 with Subsequent Concentration by Temperature Shift:

For this, 116.7 mg of docosahexaenoic acid ethyl ester (DHAEE) and 29.2 mg of docosapentaenoic acid ethyl ester The loading of the exchanger with DHAEE is 0.40% (g of DHAEE/100 g of $^+$H exchanger).

A further increase in the purity of the DHAEE on the silver-loaded cation exchanger is obtained by washing the PUFA-loaded cation exchanger with 100 ml of solvent (for example ethanol) and then heating it in a solvent (for example ethanol, acetone). The temperature range used here is between 50° C. and 80° C. (table 7).

TABLE 6

Results of attaching a mixture of DHAEE and DPAEE to Ag$^+$ Dowex ® 50 WX8

| Time (h) | S DPAEE (area %) | S DHAEE (area %) | S DPAEE (mg) | S DHAEE (mg) | Total (mg) | R in EtOH (%) | DHAEE Dowex (mg) | DPAEE Dowex (mg) | DHAEE Dowex (area %) | DHAEE yield (%) | Purification factor DHAEE |
|---|---|---|---|---|---|---|---|---|---|---|---|
| 0 | 19.3 | 77.8 | 30.2 | 118.8 | 149.0 | 101.5 | −2.1 | −0.2 | 89.6 | −1.7 | |
| 1 | 21.8 | 74.0 | 28.1 | 95 | 123.1 | 84.2 | 21.7 | 1.3 | 94.5 | 18.6 | 1.18 |
| 2 | 24.1 | 72.4 | 28.1 | 82.1 | 101.2 | 74.9 | 34.7 | 1.9 | 94.7 | 29.7 | 1.18 |
| 3.5 | 26.1 | 70.0 | 25.9 | 71.3 | 97.2 | 66.6 | 45.5 | 3.2 | 93.4 | 39.0 | 1.17 |
| 4.5 | 27.3 | 68.6 | 25.9 | 64.8 | 90.7 | 62.0 | 55.0 | 3.5 | 93.8 | 44.5 | 1.17 |
| 5.5 | 27.5 | 64.3 | 25.9 | 60.5 | 86.4 | 59.2 | 56.3 | 3.2 | 94.6 | 48.2 | 1.18 |
| 6.5 | 30.0 | 65.2 | 25.9 | 54.0 | 79.9 | 54.0 | 62.8 | 4.3 | 93.6 | 53.8 | 1.17 |
| 7.5 | 30.3 | 61.2 | 23.8 | 49.7 | 73.5 | 50.3 | 67.1 | 5.4 | 92.6 | 57.5 | 1.16 |
| 24 | 47.2 | 37.9 | 21.6 | 17.3 | 38.9 | 26.5 | 99.5 | 7.8 | 92.8 | 85.2 | 1.16 |

S: supernatant,
R = recovery,
Dowex: Dowex ® [lacuna] WX8

TABLE 7

Development of the purities of DHAEE and DPAEE in the supernatant (ethanol) during heating to differing temperatures.

| t [h] | 60° C. DPAEE [area %] | DHAEE [area %] | 70° C. DPAEE [area %] | DHAEE [area %] | 80° C. DPAEE [area %] | DHAEE [area %] |
|---|---|---|---|---|---|---|
| 0.5 | 15.3 | 84.7 | 12.5 | 87.5 | 13.4 | 86.6 |
| 1 | 18.0 | 82.0 | 15.3 | 84.7 | 15.9 | 84.1 |
| 1.5 | 21.1 | 78.9 | 17.2 | 82.8 | 18.4 | 81.6 |
| 2 | 21.9 | 78.1 | 19.1 | 80.9 | 19.1 | 80.9 |
| 2.5 | 25.0 | 75.0 | 22.3 | 77.7 | 22.6 | 77.4 |
| Product phase ACN | 5.0 | 95.0 | 4.6 | 95.4 | 4.9 | 95.3 |
| Starting material on Dowex 50 WX8 | 7.7 | 92.3 | 7.7 | 92.3 | 7.7 | 92.3 |

For this, a Pyrex tube (Pyrex borosilicate glass tubes 16×100 mm, Merck Eurolab, Darmstadt) is charged each time with 1 ml of Ag-Dowex® 50 WX8 (200-400 mesh), which has been loaded with 1.21% DHAEE (g of DHAEE/100 g of H$^+$ Dowex), and mixed with 2 ml of ethanol and mixed on the Vibromixer. The tube is then heated to 60, 70 and 80° C.) [sic] and the supernatant is analyzed by gas chromatography. The purity of the DHAEE on the Dowex at the start of the experiment was 92.3% (Dowex® 50 WX8, 200-400 mesh). After 2.5 h, it is allowed to cool, the supernatant is taken off and washed once with 2 ml of ethanol. The DHAEE is then decomplexed from the Dowex using 2 ml of ACN for 3 h.

The gas-chromatographic analysis of the ACN phase shows an enrichment of the DHAEE on the silver-loaded cation exchanger to approximately 95% in all experiments.

Since detachment of the product by acetonitrile is undesirable in many cases, other methods were developed in which the use of a toxic solvent can be avoided, or the use can be ruled out completely. These methods are explained below.

Variant C Detaching the Products from the Ag$^+$ Exchanger without ACN (FIG. 1)

In the case of complexing with PUFAs having <4 double bonds, the PUFAs can be successfully detached from the 100% silver-loaded cation exchanger just by adding a polar solvent (for example ethanol in the case of attachments in nonpolar solvents such as n-hexane) without or with simultaneous temperature increase (for example heat exchanger, heating bath, microwave, thermal block), without using ACN.

Generally, the temperatures are just below the boiling point of the solvent used. Should the PUFA be too strongly complexed, a cation exchanger can be used which is not 100% loaded with silver and therefore is unable to complex the PUFAs so strongly. In many cases, separating off the PUFAs succeeds just by using one of the abovementioned solvents without temperature shift.

EXAMPLE 9

Experimental Attachment of a Mixture of DHAEE and DPAEE to 30% Partially Silvered Ag$^+$ Amberlyst® 15 (20-50 Mesh)

For this, a mixture of 0.63 g of docosahexaenoic acid ethyl ester (DHAEE) and 0.17 g of docosapentaenoic acid ethyl ester ((ω-6 DPAEE) is added to a stirred solution of the 30% silver-loaded exchanger (10 g of H$^+$ Amberlyst® 15) in 100 ml of n-hexane. The suspension is shaken at 26° C. under a protective gas for 60 min at 100 rpm.

[lacuna] The purity of the product can likewise be determined in such a manner (table 8).

The purity of the DHAEE was increased from 80% to 90.5%. The attachment is complete after just a few minutes. The DHAEE loading of the exchanger is 2.1% (g of DHAEE/100 g of H$^+$ exchanger). The theoretical yield from the table is 32.5% of 90.5% pure DHAEE.

Detaching the product: after removing the hexane phase together with the unbound product, 100 ml of ethanol are added to the exchanger, the mixture is stirred for 30 min at room temperature and the ethanol phase is taken off. From this phase, already 176.3 mg of DHAEE (purity 87.6% area) may be isolated. The exchanger is then stirred with a further 100 ml of ethanol at 70° C. for 1 h at 300 rpm. From this phase, a further 51.6 mg of DHAEE (94.5% area) can be isolated. Fractionation of the ethanol phases, however, is not necessary. From the separated hexane phase, after removing the hexane, 379.9 mg of DHAEE were reisolated. The recovery of the bound DHAEE is greater than 96%. The combined ethanol extracts lead to 227.9 mg of DHAEE at a purity of 89.2% (area). The yield of DHAEE is 32%.

TABLE 8

Results of attaching a mixture of DHAEE and DPAEE to partially silvered Ag$^+$ Amberlyst ® 15 (20-50 mesh)

| Time (min) | S DPAEE (area %) | S DHAEE (area %) | S DPAEE (mg) | S DHAEE (mg) | Total (mg) | R in EtOH (%) | DHAEE Amberlyst (mg) | DPAEE Amberlyst (mg) | DHAEE Amberlyst (area %) | DHAEE yield (%) | Purification factor DHAEE |
|---|---|---|---|---|---|---|---|---|---|---|---|
| 0 | 19.2 | 71.5 | 161.7 | 601.3 | 763.0 | 95.4 | 29.4 | 7.7 | 79.2 | 4.7 | |
| 10 | 22.3 | 65.8 | 141.4 | 416.9 | 558.1 | 69.8 | 213.8 | 28.1 | 88.4 | 33.9 | 1.11 |

TABLE 8-continued

Results of attaching a mixture of DHAEE and DPAEE to partially silvered Ag+ Amberlyst ® 15 (20-50 mesh)

| Time (min) | S DPAEE (area %) | S DHAEE (area %) | S DPAEE (mg) | S DHAEE (mg) | Total (mg) | R in EtOH (%) | DHAEE Amberlyst (mg) | DPAEE Amberlyst (mg) | DHAEE Amberlyst (area %) | DHAEE yield (%) | Purification factor DHAEE |
|---|---|---|---|---|---|---|---|---|---|---|---|
| 30 | 22.9 | 66.0 | 151.1 | 435.5 | 586.7 | 73.3 | 195.2 | 18.3 | 91.5 | 30.9 | 1.14 |
| 60 | 22.8 | 65.7 | 147.9 | 425.6 | 573.5 | 71.7 | 205.1 | 21.5 | 90.5 | 32.5 | 1.13 |

S: supernatant;
R: recovery;
Amberlyst: Amberlyst ® 15

Variant B Detaching the Silver from the Cation Exchanger with Simultaneous Release of the Fatty Acid Ethyl Ester (FIGS. 1 and 3)

EXAMPLE 10

Regenerative Detachment of the Fatty Acid Ethyl Ester

To avoid the use of acetonitrile when detaching the DHAEE from the Ag+ Dowex®, the processes as described in FIG. 2 can be used.

After separating off the ethanolic supernatant from the reaction, the silver-loaded cation exchanger is washed silver-free with an excess of 0.4 M sodium nitrate solution ($NaNO_3$). This can be performed in a round-bottomed flask (batch) or in a glass column (continuously). At the same time, the DHAEE is released from the cation exchanger and can be decanted off from the aqueous phase as an oily phase. It is not necessary here to leach off all the silver to detach the DHAEE. However, in practice, complete detachment is the simplest method.

After separating off the product, the silver is precipitated out with a carbonate solution (e.g. $Na_2CO_3$, $K_2CO_3$ or $NaHCO_3$). The silver carbonate formed (e.g. $Ag_2CO_3$) precipitates out as a yellow precipitate and can be filtered off from the supernatant in a very simple manner. The silver carbonate is then brought into solution with stoichiometric amounts of nitric acid ($HNO_3$). This solution can be used directly for reattaching the silver.

The silver loading of the exchanger corresponds to the initial loading. The selectivity of the exchanger is retained in full.

In this manner, the detachment and isolation of the DHAEE can be performed without solvent, which is of great advantage particularly for applications in foods.

This application claims priority to German Patent Application No. 101 27 111.5, filed Jun. 5, 2001, the entirety of which is hereby incorporated by reference.

The invention claimed is:

1. A method for separating off one or more of the most highly unsaturated compound(s) from a liquid mixture additionally comprising one or more less highly unsaturated organic compound(s) and/or one or more saturated organic compound(s), comprising the steps of:
   (i) loading an acid cation exchanger with silver ions,
   (ii) mixing the acid cation exchanger with a liquid mixture,
   (iii) stirring in a batch method, the liquid mixture at a temperature which is below the boiling point of the solvent used,
   (iv) separating off a supernatant,
   (v) detaching from the acid cation exchanger the less highly unsaturated organic compound(s) by adding a solvent selected from the group consisting of ketones, alcohols or a mixture of such solvents, and separating off, and
   (vi) detaching the most highly unsaturated compound(s) from the acid cation exchanger by detaching the silver ions from the acid cation exchanger.

2. The method as claimed in claim 1, characterized in that the most highly unsaturated compound is a polyunsaturated fatty acid having at least two double bonds.

3. The method as claimed in claim 2, characterized in that the polyunsaturated fatty acid is selected from the group consisting of hexadecadienoic acids, hexadecatrienoic acids, hexadecatetraenoic acids, linoleic acid, γ-linolenic acid, α-linolenic acid, stearidonic acid, arachidonic acid, eicosatrienoic acids, eicosatetraenoic acids, eicosapentaenoic acids, docosapentaenoic acids, docosahexaenoic acid, tetracosadienoic acids, octacosaoctaenoic acids.

4. The method as claimed in claim 1, characterized in that the less highly unsaturated compound(s) is (are) detached from the cation exchanger by adding a solvent selected from the group consisting of ketones, alcohols, or a mixture thereof.

5. The method as claimed in claim 4, characterized in that the less highly unsaturated compound(s) is (are) detached from the cation exchanger by adding methanol or ethanol.

6. The method as claimed in claim 4, characterized in that the most highly unsaturated compound(s) is (are) detached from the cation exchanger at a temperature range from −20° C. to 80° C.

7. The method as claimed in claim 1, characterized in that the liquid mixture comprises a solvent.

8. The method as claimed in claim 7, characterized in that the solvent is selected from the group consisting of ethers, esters, ketones, alkanes and alcohols.

9. The method as claimed in claim 7, characterized in that the solvent is selected from the group consisting of n-hexane, n-heptane, n-pentane, ethanol and methanol.

10. The method as claimed in claim 1, characterized in that the most highly unsaturated compound(s) is (are) detached from the cation exchanger by detaching the silver from the ion exchanger by adding sodium nitrate.

11. The method as claimed in claim 1, characterized in that the liquid mixture comprises a saturated fatty acid and/or an unsaturated fatty acid containing n double bonds and/or a fatty acid containing n+I or more double bonds, where the fatty acid containing n+I or more double bonds is separated from the saturated fatty acid or the unsaturated fatty acid containing n double bonds, where n is an integer between 1 and 10.

12. The method as claimed in claim 1, characterized in that the liquid mixture comprises crude ester mixtures, processed oils, ester mixtures, fatty acid mixtures and/or derivatives of polyunsaturated fatty acids.

13. The method as claimed in claim 1, characterized in that the liquid mixture comprises fish oils, vegetable oils and/or microbial oils.

14. The method as claimed in claim 1, characterized in that the acid cation exchanger is a gel which has as parent substance styrene with divinylbenzene branches, has sulfonic acid and/or carboxyl groups as active silver-bearing groups and is microporous or macroporous.

15. The method as claimed in claim 1, characterized in that the acid cation exchanger is loaded by treatment with silver nitrate.

16. The method as claimed in claim 1, characterized in that the mixture of loaded cation exchanger with the liquid mixture is stirred at elevated temperature.

17. The method as claimed in claim 16, characterized in that the temperature is elevated by the action of an external heat source, by microwaves, ultrasound or electromagnetic radiation.

18. The method as claimed in claim 1, characterized in that the most highly unsaturated compound(s) is (are) detached from the cation exchanger by adding methanol or ethanol.

19. The method as claimed in claim 1, characterized in that the most highly unsaturated compound(s) has (have) at least 4 double bonds.

20. The method as claimed in claim 1, characterized in that the acid cation exchanger is completely loaded with silver ions.

21. A method for separating off one or more of the most highly unsaturated compound(s) from a liquid mixture additionally comprising one or more less highly unsaturated organic compound(s) and/or one or more saturated organic compound(s), comprising the steps of:

(i) loading an acid cation exchanger with silver ions, (ii) mixing the acid cation exchanger with a liquid mixture, (iii) stirring in a batch method, the liquid mixture at a temperature which is below the boiling point of the solvent used, (iv) separating off a supernatant, (v) detaching from the acid cation exchanger the less highly unsaturated organic compound(s) by adding a solvent selected from the group consisting of ketones, alcohols or a mixture of such solvents, and separating off, and (vi) detaching the most highly unsaturated compound(s) from the acid cation exchanger where the liquid mixture comprises at least one polyunsaturated fatty acid containing at least 4 double bonds and the acid cation exchanger is completely loaded with silver ions and the most highly unsaturated compound(s) is (are) detached from the cation exchanger by detaching the silver ions.

22. The method as claimed in claim 21, characterized in that the silver ions are detached from the cation exchanger by adding sodium nitrate.

* * * * *